(12) United States Patent
Kawakami et al.

(10) Patent No.: US 8,597,212 B2
(45) Date of Patent: Dec. 3, 2013

(54) WRIST ASSISTING APPARATUS

(75) Inventors: Takashi Kawakami, Ehime (JP); Toshihiko Ishiko, Ehime (JP); Keisuke Ueda, Osaka (JP)

(73) Assignee: Panasonic Corporation, Osaka (JP)

( * ) Notice: Subject to any disclaimer, the term of this patent is extended or adjusted under 35 U.S.C. 154(b) by 732 days.

(21) Appl. No.: 12/755,651

(22) Filed: Apr. 7, 2010

(65) Prior Publication Data
US 2010/0249948 A1 Sep. 30, 2010

(51) Int. Cl.
*A61F 5/00* (2006.01)

(52) U.S. Cl.
USPC ........ 601/40; 601/5; 601/23; 601/33; 602/16; 602/21

(58) Field of Classification Search
USPC ........... 601/5, 23, 24, 26, 33, 40, 84, 97, 101, 601/103, 148–150; 602/20–23; 623/26, 62; 482/47, 49
See application file for complete search history.

(56) References Cited

U.S. PATENT DOCUMENTS

| | | | | |
|---|---|---|---|---|
| 5,254,078 A | * | 10/1993 | Carter et al. | 602/21 |
| 5,653,680 A | * | 8/1997 | Cruz | 602/21 |
| 6,689,074 B2 | * | 2/2004 | Seto et al. | 601/5 |
| 2004/0267331 A1 | * | 12/2004 | Koeneman et al. | 607/49 |

FOREIGN PATENT DOCUMENTS

| | | |
|---|---|---|
| JP | 2004-105263 A | 4/2004 |
| JP | 2007-167484 A | 7/2007 |
| WO | WO 2007/043308 A1 | 4/2007 |

* cited by examiner

*Primary Examiner* — Quang D Thanh
(74) *Attorney, Agent, or Firm* — RatnerPrestia

(57) ABSTRACT

A wrist assisting apparatus can smoothly bend and stretch a joint even if a turning shaft of a joint and a rotation shaft of a wearing tool are deviated from each other. Also, an excessive load is not applied to a user. The wrist assisting apparatus of the present invention includes a palm support member for supporting a hand, angle changing members connected to sides of the palm support member, a front arm wearing tool disposed along the front arm, and joint members for forming a rotation shaft of the angle changing member with respect to the front arm wearing tool, wherein the angle changing members are provided on both sides of the palm support member, the joint members are provided on the angle changing members, respectively, and the joint members are located on both sides of a wrist.

12 Claims, 12 Drawing Sheets

WRIST ASSISTING APPARATUS

TECHNICAL FIELD

The present invention relates to a wrist assisting apparatus that assists a wrist motion of a user.

BACKGROUND TECHNIQUE

There is proposed a power apparatus having a tube that is restrained in its longitudinal direction and is expanded in its radial direction by charging gas, liquid, or solid material, or a mixture thereof into the tube, wherein a cylindrical sleeve that expands and contracts in the longitudinal direction and the radial direction is disposed outside the tube, both ends of the apparatus are restrained, the one of the ends of the apparatus is provided with a charging opening, and the tube is made of one of polyester-based material, polyamide-based material, polyethylene-based material, polyimide-based material, polystyrene-based material, and polycarbonate-based material, or a film or fiber having mixture thereof (patent document 1).

A motion assisting apparatus utilizing this kind of power apparatus is also proposed (patent documents 2 and 3).

In the patent document 2, the apparatus also assists a twisting motion of an elbow joint in addition to the bending and stretching motion of the elbow joint by carrying out the bending and stretching motion of the elbow joint using a joint made of elastic body.

[Patent Document 1] Japanese Patent Application Laid-open No. 2004-105263
[Patent Document 2] International Patent Application Laid-open No. 2007/043308
[Patent Document 3] Japanese Patent Application Laid-open No. 2007-167484

DISCLOSURE OF THE INVENTION

For example, when a wearing tool that is worn on a palm portion and a wearing tool that is worn on a front arm are connected to each other through a single-axis rotation shaft, if a turning shaft of a joint and the rotation shaft of the wearing tool are deviated from each other when wearing, or when the turning shaft of the joint and the rotation shaft of the wearing tool are deviated from each other as a result of bending motion after they were worn, the joint can not sufficiently bend or stretch, and an excessive load is applied to a user in some cases. A relative distance between the palm and the front arm is varied by the bending and stretching motion, but a distance between the wearing tools is not varied. This means that the wearing tool is deviated from an arm or a palm of a user, the wearing feeling is inferior, and if the wearing tool is used for a long time, this phenomenon causes rubbing and pain.

According to a joint shown in the patent document 2, the rotation shaft has two axes by the joint, and a deviation of the joint with respect to the turning shaft can be moderated as compared with the single axis rotation shaft. A deviation of the wearing tool can also be moderated. However, since the distance between the wearing tools is fixed and it is difficult to align the joint with an ideal position, a deviation of shafts or a deviation of the wearing tools can not completely be corrected. With mere double joints, since the joints are independent from each other, a motion thereof is unstable and there is a risk that the joint buckles. Since the joint of the patent document 2 is made of elastic body, the joint can flexibly follow a deviation of the shafts or the wearing tools, and even if a load such as twisting motion is applied to the joint, the joint can accept the load, but in order to sufficiently withstand the repeated load for a long term, material of the elastic body must be selected precisely.

The present invention has been accomplished to solve such a conventional problem, and it is an object of the invention to provide a wrist assisting apparatus that can smoothly bend and stretch a joint even if a turning shaft of the joint and a rotation shaft of a wearing tool are deviated from each other, and that does not apply an excessive load to a user.

A first aspect of the present invention provides a wrist assisting apparatus comprising a palm support member for supporting a hand, angle changing members connected to sides of the palm support member, a front arm wearing tool disposed along the front arm, and joint members for forming a rotation shaft of the angle changing member with respect to the front arm wearing tool, wherein the angle changing members are provided on both sides of the palm support member, the joint members are provided on the angle changing members, respectively, and the joint members are located on both sides of a wrist.

According to a second aspect, in the wrist assisting apparatus of the first aspect, the palm support member is a palm rest member for supporting a side of a back of the hand.

According to a third aspect, in the wrist assisting apparatus of the first aspect, the palm support member is a palm grasping member for supporting a palm side.

According to a fourth aspect, in the wrist assisting apparatus of the first aspect, the front arm wearing tool and the angle changing member are connected to each other through an actuator that drives in straight lines.

According to a fifth aspect, in the wrist assisting apparatus of the fourth aspect, an artificial muscle that expands and contracts by supplying or discharging gas, liquid, or solid material, or a mixture thereof is used as the actuator.

According to a sixth aspect, in the wrist assisting apparatus of the first aspect, two artificial muscles are used for each of the angle changing members for connecting the front arm wearing tool and the angle changing member with each other, and an actuator that expands and contracts by supplying or discharging gas, liquid, or solid material, or a mixture thereof is used as the artificial muscle.

According to a seventh aspect, in the wrist assisting apparatus of the sixth aspect, an axis connecting a fulcrum of the angle changing member and a fulcrum of a non-driving side artificial muscles on the side of the front arm wearing tool in the two artificial muscles with each other does not move toward a driving side beyond the rotation shaft of the joint member.

According to an eighth aspect, the wrist assisting apparatus of the sixth aspect further includes a first link member that turns around a palm side position of the angle changing member and a second link member that turns around a side of a back of the hand portion of the angle changing member, wherein the artificial muscles are respectively connected to an end of the first link member and an end of the second link member.

According to a ninth aspect, in the wrist assisting apparatus of the eighth aspect, an axis connecting a turning fulcrum of the link member on the side of the angle changing member and a fulcrum of a non-driving side artificial muscle on the side of the front arm wearing tool in the two artificial muscles with each other does not move toward a driving side beyond the rotation shaft of the joint member.

According to a tenth aspect, in the wrist assisting apparatus of the eighth aspect, the rotation shaft of the joint member is disposed closer to the front arm wearing tool than a phantom line connecting the turning fulcrum of the first link member and the turning fulcrum of the second link member with each other, and a substantially center portion of the joint member in its longitudinal direction is defined as a joint position of the wrist.

According to an eleventh aspect, the wrist assisting apparatus of the first aspect further includes a moving mechanism for moving the palm support member toward or away from the front arm.

According to a twelfth aspect, the wrist assisting apparatus of the second aspect further includes a belt provided on an upper surface of the palm rest member, and a moving mechanism for moving the belt toward or away from the front arm.

According to a thirteenth aspect, in the wrist assisting apparatus of the third aspect, moving mechanisms for moving the palm grasping member toward or away from the front arm, and turning shafts for changing angle with respect to the moving mechanisms are provided on both ends of the palm grasping member, and the turning shaft can displace with respect to the palm grasping member.

According to a fourteenth aspect, in the wrist assisting apparatus of the third aspect, a belt fixing tool is provided on an upper surface or a lower surface of the palm grasping member.

According to a fifteenth aspect, in the wrist assisting apparatus of the third aspect, a palm rest member is provided on an upper surface or a lower surface of the palm grasping member.

According to the present invention, since both sides of the wrist are supported by the pair of joint members, the wrist can smoothly move, and the wrist can strongly be held.

According to the wrist assisting apparatus of the first aspect of the invention, the angle changing members are provided on both sides of the palm support member, the joint members are provided on the angle changing members, respectively, and the joint members are located on both sides of the wrist. With this embodiment, since the both sides of the wrist are supported by the pair of joint members, the wrist can smoothly move, and the wrist can strongly be held.

According to the second aspect of the invention, in the wrist assisting apparatus of the first aspect, the palm support member is the palm rest member for supporting the side of the back of the hand. With this embodiment, the palm can bend normally and backward without hindering the palm motion.

According to the third aspect of the invention, in the wrist assisting apparatus of the first aspect, the palm support member is the palm grasping member for supporting the palm side. With this embodiment, play between the apparatus and the hand can be eliminated, and sufficient backward bending region can be secured as compared with the case where the palm rest member is used.

According to the fourth aspect of the invention, in the wrist assisting apparatus of the first aspect, the front arm wearing tool and the angle changing member are connected to each other through an actuator that drives in straight lines. With this embodiment, it is possible to assist the wrist motion even if the actuator that drives in straight lines is used.

According to the fifth aspect of the invention, in the wrist assisting apparatus of the fourth aspect, an artificial muscle that expands and contracts by supplying or discharging gas, liquid, or solid material, or the mixture thereof is used as the actuator. With this embodiment, it is possible to realize a motion close to a human muscle, and the rehabilitation effect is enhanced.

According to the sixth aspect of the invention, in the wrist assisting apparatus of the first aspect, two artificial muscles are used for each of the angle changing members for connecting the front arm wearing tool and the angle changing member with each other, and an actuator that expands and contracts by supplying or discharging gas, liquid, or solid material, or a mixture thereof is used as the artificial muscle. With this embodiment, the wrist can bend toward both the palm side and the backhand side.

According to the seventh aspect of the invention, in the wrist assisting apparatus of the sixth aspect, the axis connecting the fulcrum of the angle changing member and the fulcrum of the non-driving side artificial muscles on the side of the front arm wearing tool in the two artificial muscles with each other does not move toward the driving side beyond the rotation shaft of the joint member. With this embodiment, the wrist can smoothly bend from the palm side toward the backhand side or from the backhand side toward the palm side.

According to the eighth aspect of the invention, the wrist assisting apparatus of the sixth aspect further includes the first link member that turns around the palm side position of the angle changing member and the second link member that turns around the side of the back of the hand portion of the angle changing member, wherein the artificial muscles are respectively connected to an end of the first link member and an end of the second link member. With this embodiment, the wrist can smoothly bend toward the palm side and the backhand side. It is possible to prevent a sag of the artificial muscle in its initial state, to prevent a bracing when the wrist starts bending or stretching in one direction after the wrist bended or stretched in the opposite direction, and the wrist can displace largely with a small shrinkage ratio of the artificial muscle.

According to the ninth aspect of the invention, in the wrist assisting apparatus of the eighth aspect, an axis connecting the turning fulcrum of the link member on the side of the angle changing member and the fulcrum of non-driving side artificial muscle on the side of the front arm wearing tool in the two artificial muscles with each other does not move toward the driving side beyond the rotation shaft of the joint member. With this embodiment, the wrist can smoothly bend from the palm side toward the backhand side or from the backhand side toward the palm side.

According to the tenth aspect of the invention, in the wrist assisting apparatus of the eighth aspect, the rotation shaft of the joint member is disposed closer to the front arm wearing tool than the phantom line connecting the turning fulcrum of the first link member and the turning fulcrum of the second link member with each other, and the substantially center portion of the joint member in its longitudinal direction is defined as the joint position of the wrist. With this embodiment, the position of the wrist joint and the position of the joint member of the apparatus can be aligned with each other, and the smooth motion can be realized.

According to the eleventh aspect of the invention, the wrist assisting apparatus of the first aspect further includes the moving mechanism for moving the palm support member toward or away from the front arm. With this embodiment, it is possible to eliminate such a sense of disharmony that a user feels as if his or her hand is pressed toward the front arm or pulled in a direction separating from the front arm.

According to the twelfth aspect of the invention, the wrist assisting apparatus of the second aspect further includes the belt provided on an upper surface of the palm rest member, and the moving mechanism for moving the belt toward or away from the front arm. With this embodiment, it is possible to eliminate such a sense of disharmony that a user feels as if his or her hand is pressed toward the front arm or pulled in a direction separating from the front arm.

According to the thirteenth aspect of the invention, in the wrist assisting apparatus of the third aspect, the moving mechanisms for moving the palm grasping member toward or away from the front arm, and the turning shafts for changing angle with respect to the moving mechanisms are provided on both ends of the palm grasping member, and the turning shaft can displace with respect to the palm grasping member. With this embodiment, since the angle of the palm grasping member can be changed, it is easy to grasp the palm grasping member, and even when a wrist is crooked due to an accident, the palm grasping member can be adapted in a sustainable way.

According to the fourteenth aspect of the invention, in the wrist assisting apparatus of the third aspect, the belt fixing tool is provided on an upper surface or the lower surface of the palm grasping member. With this embodiment, even when a grasping power is weakened, the wrist can be supported by the belt.

According to the fifteenth aspect of the invention, in the wrist assisting apparatus of the third aspect, the palm rest member is provided on an upper surface or the lower surface of the palm grasping member. With this embodiment, even when a grasping power is weakened, the wrist can be supported from the back side of the hand.

BEST MODE FOR CARRYING OUT THE INVENTION

An embodiment of the wrist assisting apparatus according to the present invention will be explained.

Figure 1:
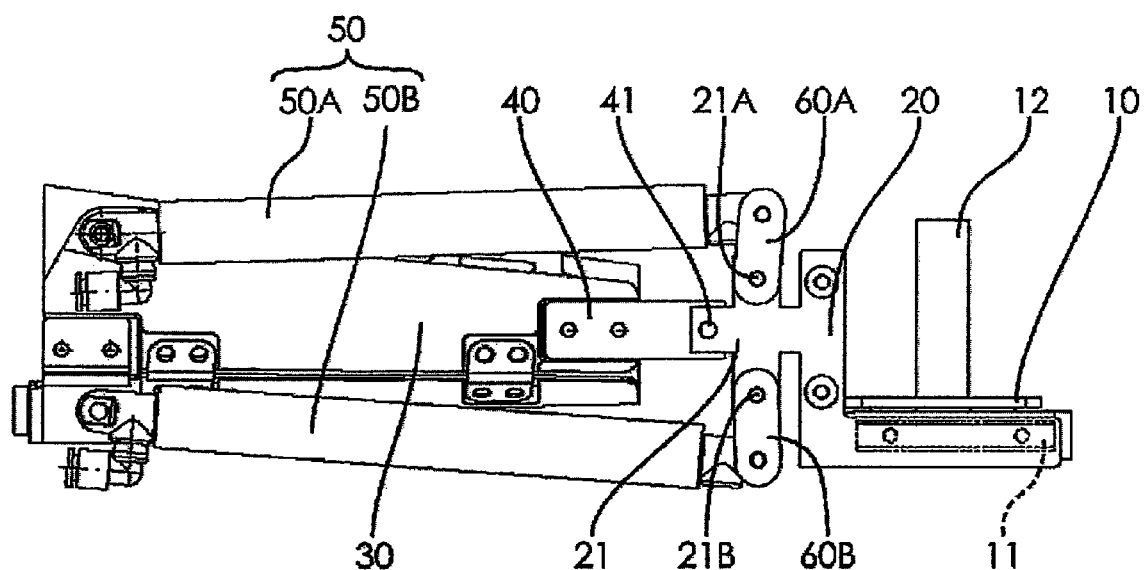
FIG. 1 is a schematic side view showing a structure of a wrist assisting apparatus according to an embodiment of the present invention.
Figure 2:
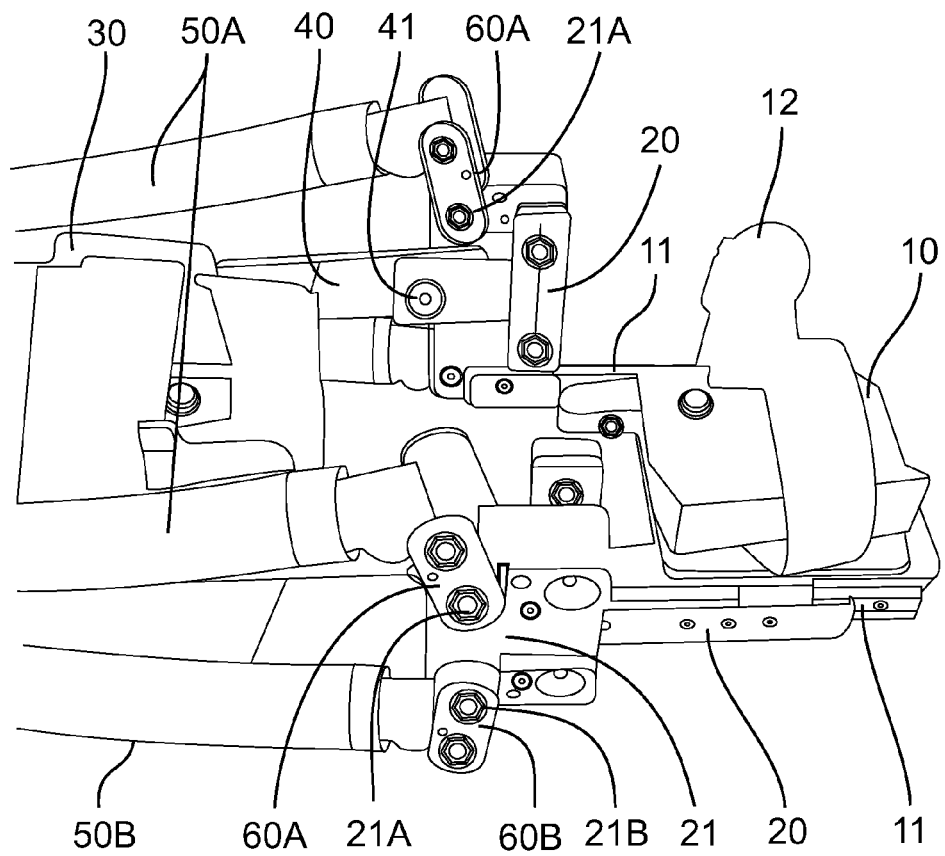
FIG. 2 is a perspective view showing the wrist assisting apparatus.
Figure 3:
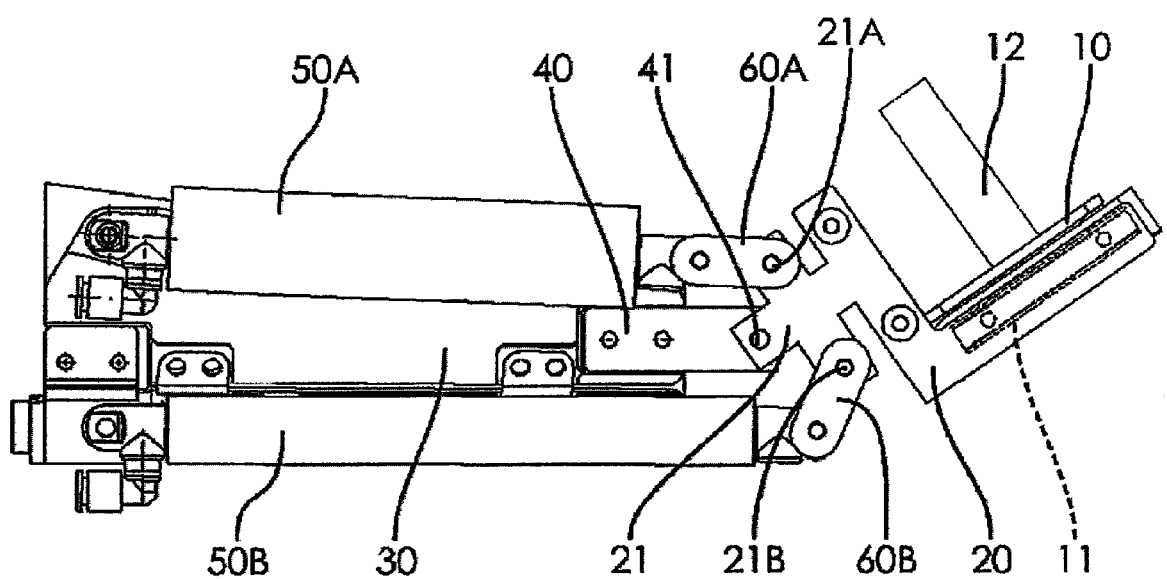
FIG. 3 is a diagram showing a structure of the wrist assisting apparatus in its palm-bending state.
Figure 4:
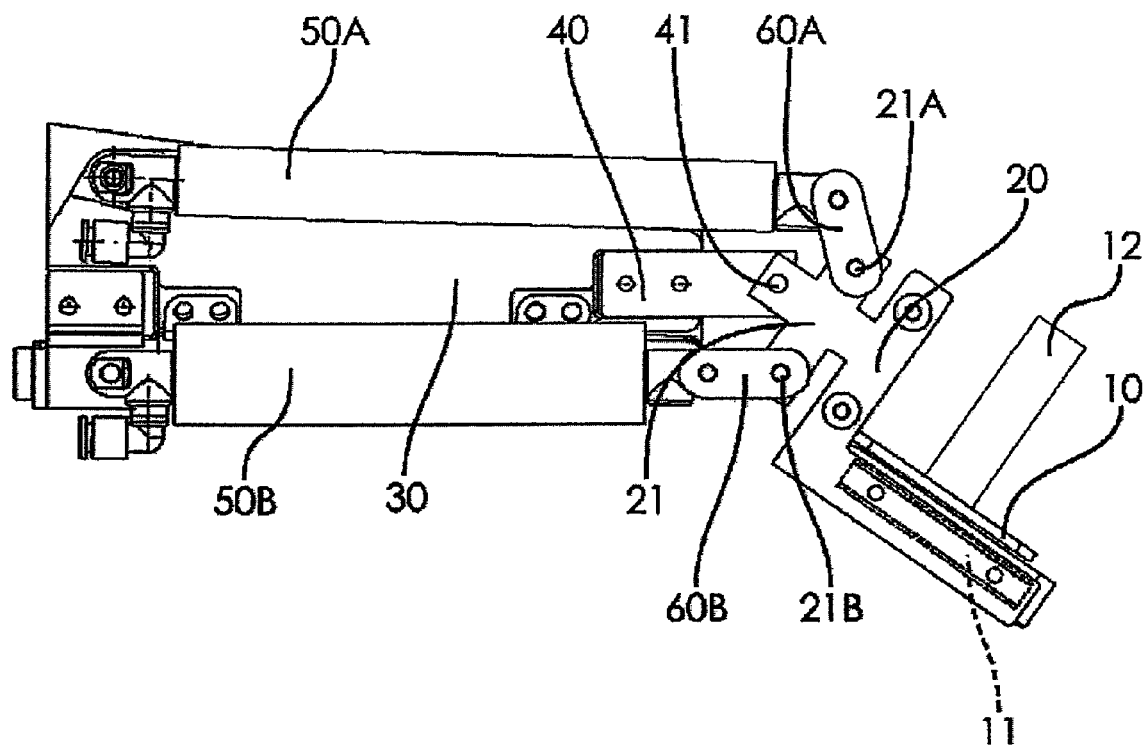
FIG. 4 is a diagram showing a structure of the wrist assisting apparatus in its backward-bending state.

FIG. 1 is a schematic side view showing a structure of the wrist assisting apparatus according to the embodiment of the present invention. FIG. 2 is a perspective view showing the wrist assisting apparatus. FIG. 3 is a diagram showing a structure of the wrist assisting apparatus in its palm-bending state. FIG. 4 is a diagram showing a structure of the wrist assisting apparatus in its backward-bending state.

The wrist assisting apparatus of the embodiment includes a palm rest member (palm support member) 10 that supports a back of a hand, angle changing members 20 connected to sides of the palm rest member 10, a front arm wearing tool 30 disposed along a front arm, and joint members 40 that form rotation shafts 41 around which the angle changing members 20 turn with respect to the front arm wearing tool 30.

The angle changing members 20 include a pair of substantially L-shaped members that are provided on both sides of the palm rest member 10, respectively. The joint members 40 are respectively provided for the angle changing members 20. The joint members 40 are located on both sides of a wrist.

The front arm wearing tool 30 and the angle changing members 20 are connected to each other through artificial muscles 50. The artificial muscle 50 is an actuator that extends and contracts at least in its longitudinal direction by supplying or discharging gas, liquid, or solid material, or a mixture thereof. As shown in the drawings, each angle changing member 20 is connected to the front arm wearing tool 30 using two artificial muscles 50A and 50B. Another mechanism can be used as the actuator only if it drives the front arm wearing tool 30 and the angle changing members 20 in straight lines.

A belt 12 is provided on an upper surface of the palm rest member 10, and a hand is held by the belt 12. The palm rest member 10 having the belt 12 includes a moving mechanism 11 that moves toward and away from the front arm. By moving the palm rest member 10 toward and away from the front arm, it is possible to eliminate such a sense of disharmony that a user feels as if his or her hand is pressed toward the front arm or pulled in a direction separating from the front arm, a deviation that can not be adjusted in terms of design can be absorbed, tolerance to a difference in physical size is increased, and fine adjustment on an individual basis becomes unnecessary.

A connecting member 21 is provided on the angle changing member 20 on the side of the front arm. One end of a first link member 60A turns around a palm-side position 21A of the connecting member 21, and the other end of a second link member 60B turns around a side of the back of the hand position (backhand-side position, hereinafter) 21B of the connecting member 21. The artificial muscle 50A is turnably connected to the other end of the first link member 60A, and the artificial muscle 50B is turnably connected to the other end of the second link member 60B.

The rotation shaft of the joint member 40 is disposed closer to the front arm wearing tool 30 than a phantom line connecting the palm-side position 21A around which the first link member 60A turns and the backhand-side position 21B around which the second link member 60B turns with each other. A position near substantially a center of the joint member 40 in its longitudinal direction is a joint position of the wrist.

According to the embodiment, a variation of a large angle can be obtained with a small displacement (shrinkage ratio) of the artificial muscle, the position of the wrist joint and the position of the joint member can be aligned with each other, and a smooth motion can be realized.

Although it is not illustrated in the drawings, the apparatus includes a power source for contracting the artificial muscles 50. It is preferable that a pair of artificial muscles 50 are provided on both sides of each arm.

The operation of the wrist assisting apparatus according to the embodiment will be explained.

In a state shown in FIG. 1, the palm is held horizontally.

If one of the artificial muscles 50A is contracted from the state shown in FIG. 1, the angle changing member 20 is displaced with respect to the front arm wearing tool 30 as shown in FIG. 3, and the palm rest member 10 can be bent toward the palm side together with the angle changing member 20.

If the other artificial muscle 50B is contracted from the state shown in FIG. 1, the angle changing member 20 can be displaced with respect to the front arm wearing tool 30 as shown in FIG. 4, and the palm rest member 10 can be bent toward the back of the hand together with the angle changing member 20.

Figure 5:
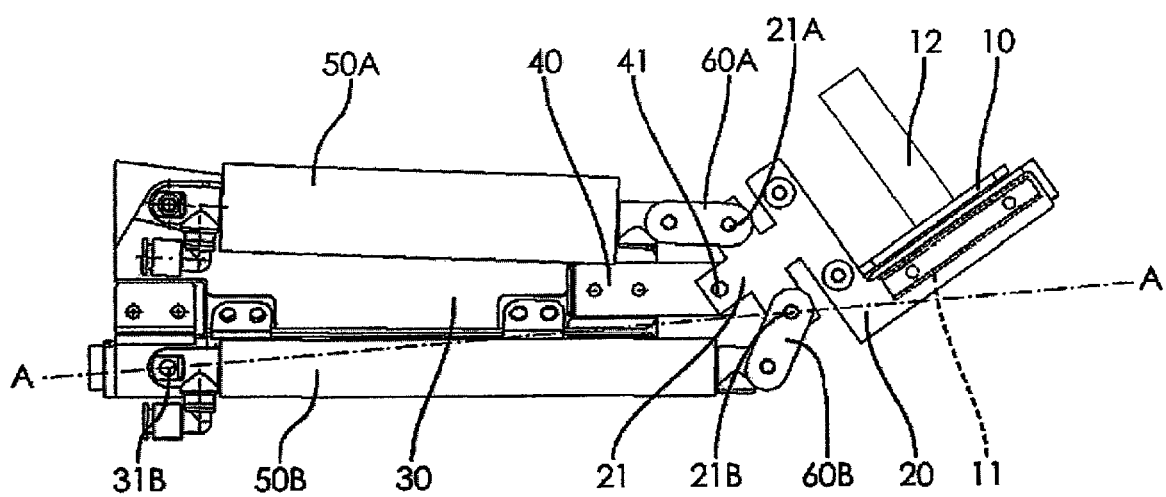
FIG. 5 is a diagram showing a relation between a rotation shaft of a joint member and an axis A connecting a turning fulcrum of a link member and a fulcrum of a non-driving side artificial muscle of the wrist assisting apparatus on the side of a front arm wearing tool with each other.

FIG. 5 shows a relation between the rotation shaft of the joint member and an axis A connecting a turning fulcrum of the link member and a fulcrum of non-driving side artificial muscle 50 of the wrist assisting apparatus on the side of the front arm wearing tool with each other.

According to the wrist assisting apparatus of the embodiment, the axis A connecting a turning fulcrum 21B of the second link member 60B on the side of the angle changing member 20 and a fulcrum 31B of the non-driving side artificial muscle 50B on the side of the front arm wearing tool in the two artificial muscles 50A and 50B with each other does not move toward a driving side beyond the rotation shaft 41 of the joint member 40 as shown in FIG. 5. According to this embodiment, the wrist can smoothly bend from the palm side toward the backhand side or from the backhand side toward the palm side.

Although the connecting member 21 is integrally formed with the angle changing member 20 in the embodiment, the connecting member 21 and the angle changing member 20 may be independent from each other.

The wrist assisting apparatus of the embodiment includes the moving mechanism 11 that moves the side surface of the palm rest member 10 toward or away from the front arm. With this, it is possible to eliminate such a sense of disharmony that a user feels as if his or her hand is pressed toward the front arm or pulled in a direction separating from the front arm.

According to an actual human motion, if a wrist is bent in a state where a palm is oriented upward, the palm inclines inward (toward a body) with respect to an axis of a front arm and the palm is bent normally or backward. To imitate the actual bending motion of the wrist, in the wrist assisting apparatus of both the embodiments, it is preferable that palm portion related members including the artificial muscle, the joint member, the angle changing member and the palm rest member are mounted in a state where they are slightly twisted inward (toward the body) with respect to the axis of the front arm relative to the front arm.

Figure 6:
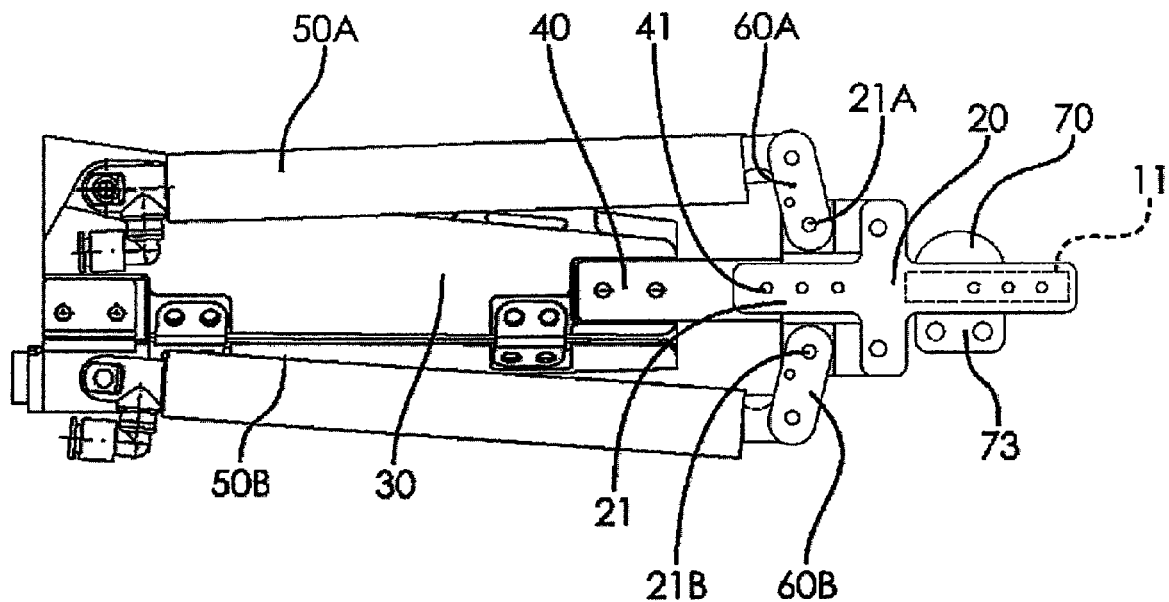
FIG. 6 is a schematic side view showing a structure of the wrist assisting apparatus of another embodiment of the invention.
Figure 7:
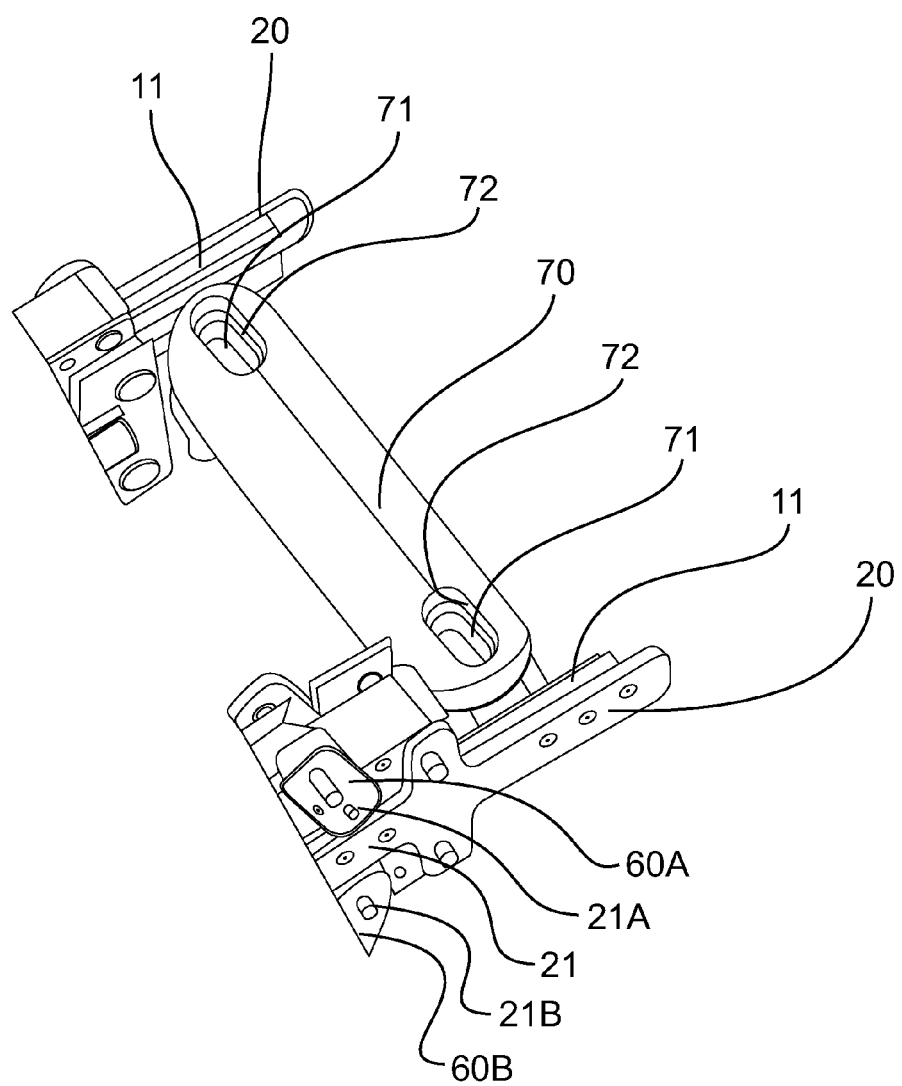
FIG. 7 is a perspective view showing an essential portion of the wrist assisting apparatus as viewed from above.
Figure 8:
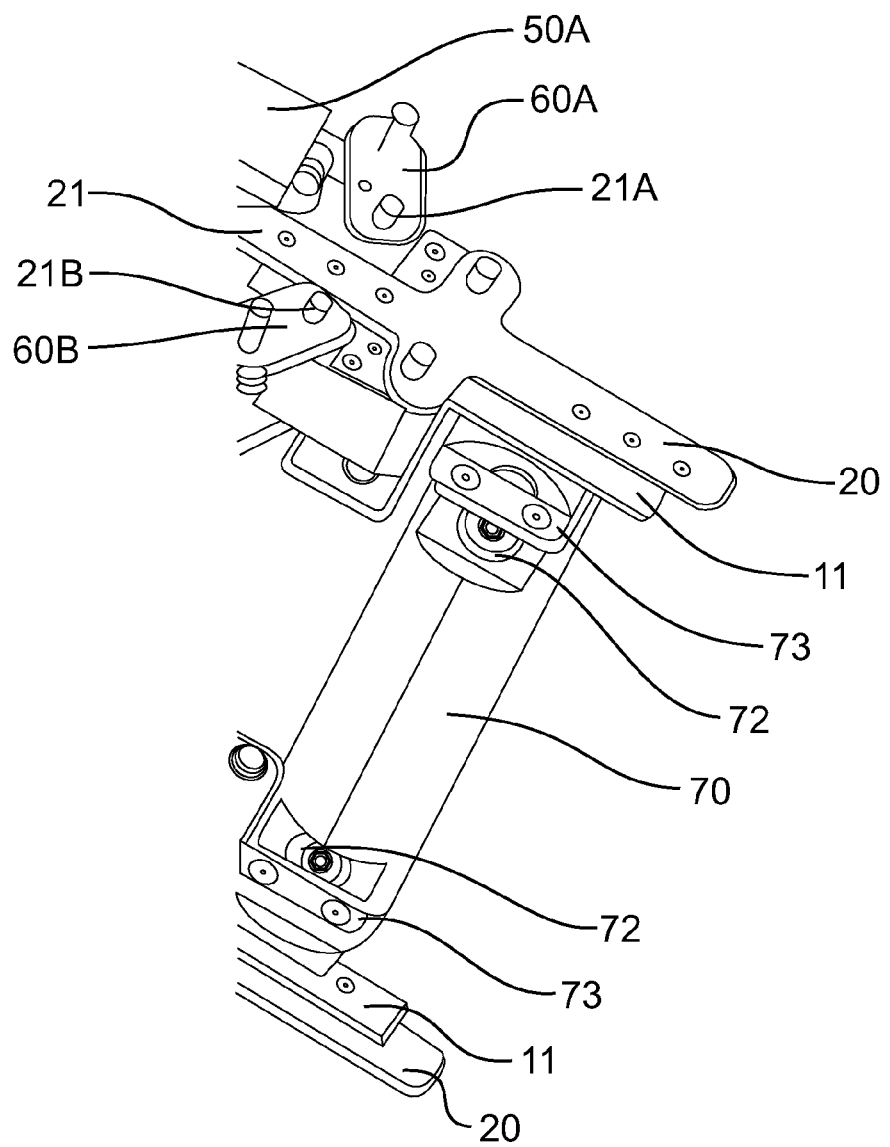
FIG. 8 is a perspective view showing the essential portion as viewed from below.
Figure 9:
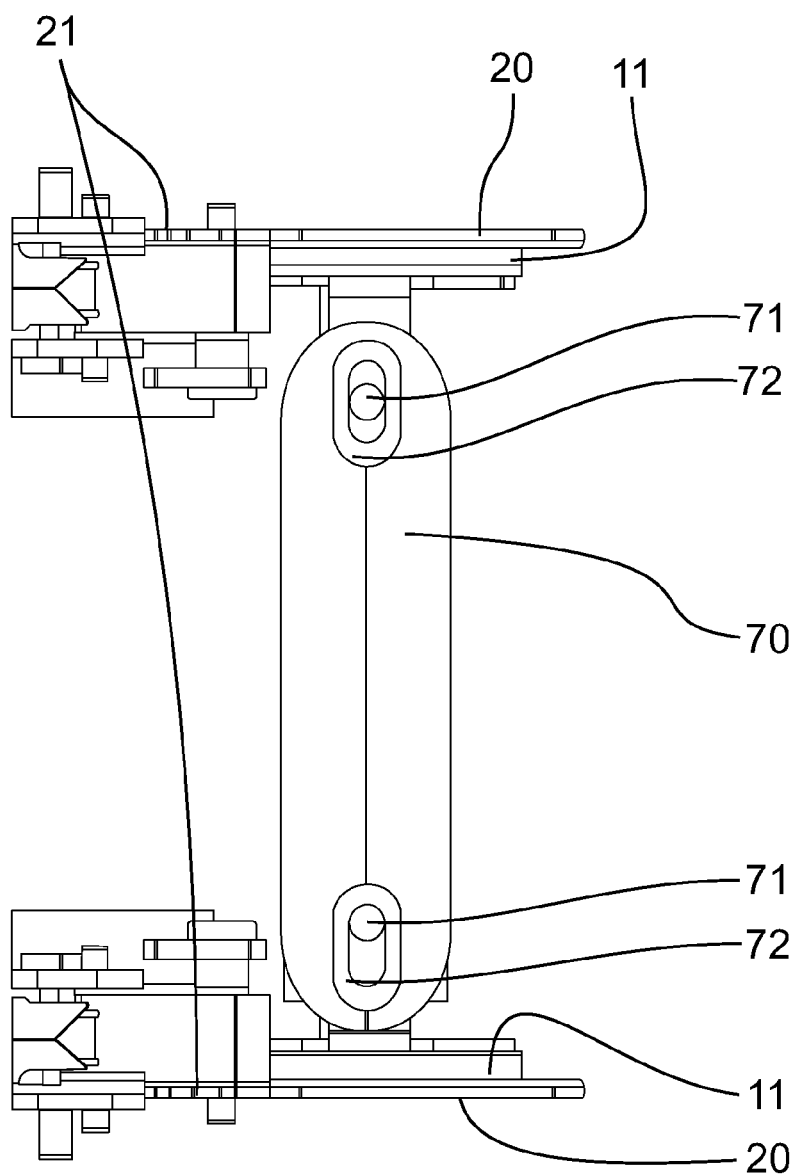
FIG. 9 is a bottom view showing the essential portion.
Figure 10:
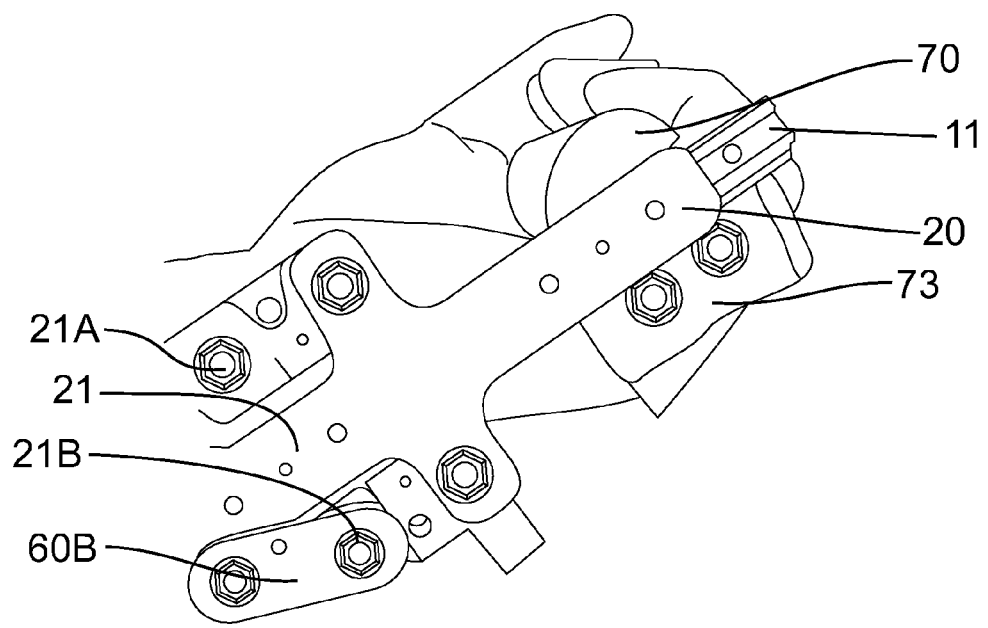
FIG. 10 is a side view of an essential portion showing a using state of the wrist assisting apparatus.
Figure 11:
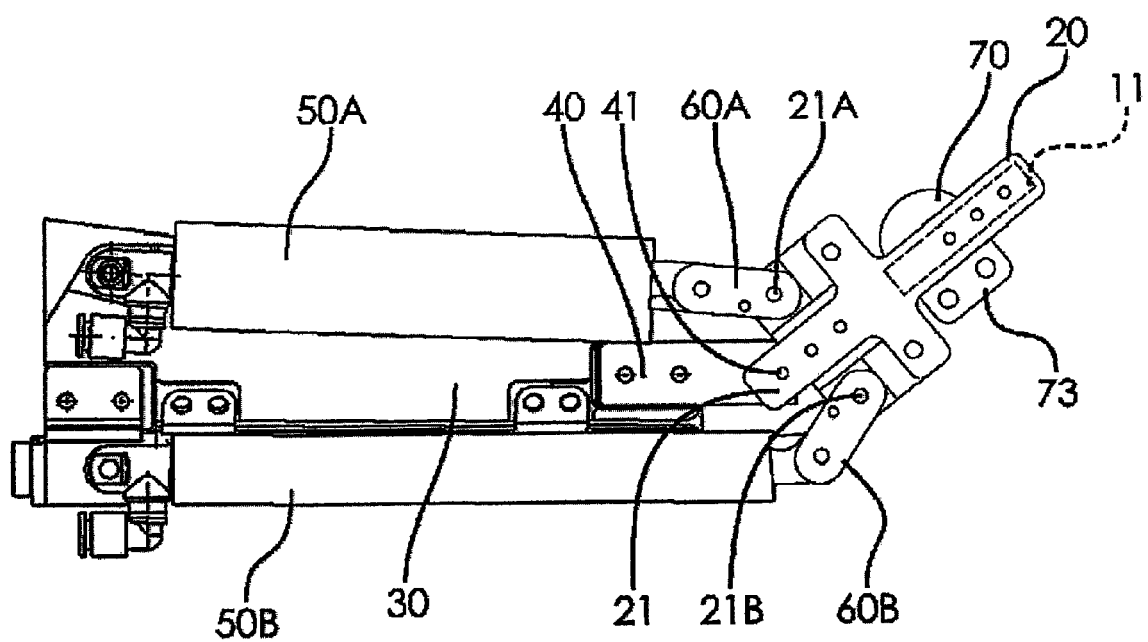
FIG. 11 is a side view showing the wrist assisting apparatus in its palm-bending state.
Figure 12:
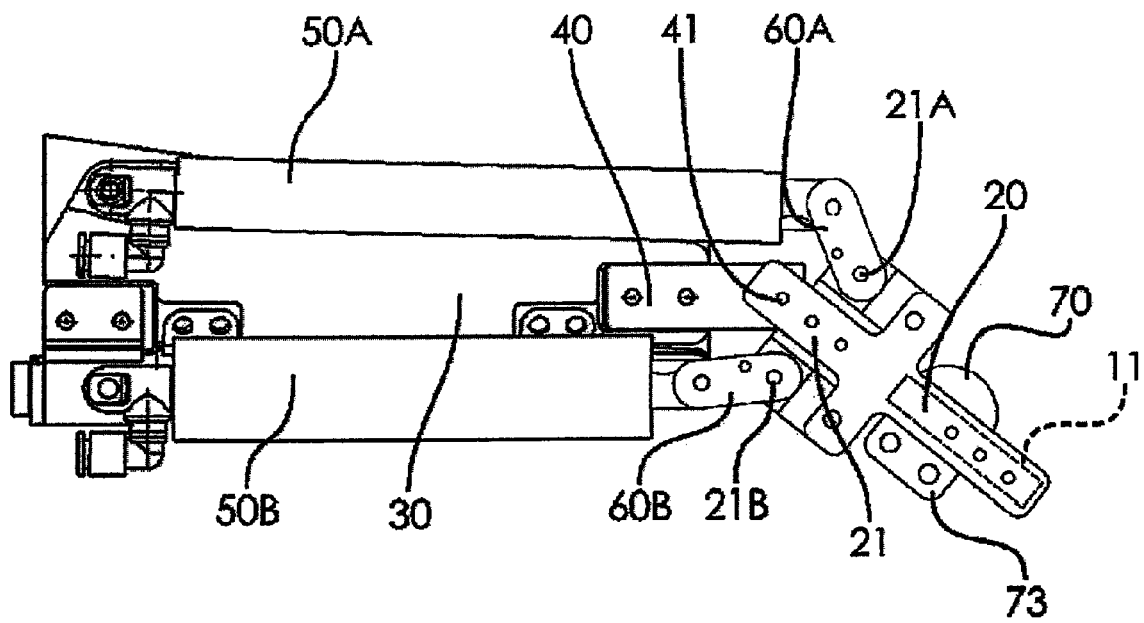
FIG. 12 is a side view showing the wrist assisting apparatus in its backward-bending state.

Next, a wrist assisting apparatus of another embodiment of the present invention will be explained based on FIGS. 6 to 12. FIG. 6 is a schematic side view showing a structure of the wrist assisting apparatus. FIG. 7 is a perspective view showing an essential portion of the wrist assisting apparatus as viewed from above. FIG. 8 is a perspective view showing the essential portion as viewed from below. FIG. 9 is a bottom view showing the essential portion. FIG. 10 is a side view of an essential portion showing a using state of the wrist assisting apparatus. FIG. 11 is a side view showing the wrist assisting apparatus in its palm-bending state. FIG. 12 is a side view showing the wrist assisting apparatus in its backward-bending state. The same constituent elements as those of the previous embodiment are designated with the same symbols, and explanation thereof will be omitted.

According to the wrist assisting apparatus of the embodiment, the connecting member 21 is connected to the angle changing member 20, and one ends of the first link member 60A and the second link member 60B are turnably mounted on the connecting member 21.

The wrist assisting apparatus of the embodiment includes a palm grasping member (palm support member) 70 instead of the palm rest member 10. Moving mechanisms 11 that moves the palm grasping member 70 toward or away from the front arm are mounted on both ends of the palm grasping member 70. The palm grasping member 70 and the moving mechanisms 11 are connected to each other through turning shafts 71, and each turning shaft 71 is provided in a long hole 72 so that an angle of the palm grasping member 70 can be changed with respect to the moving mechanism 11. Belt fixing tools 73 are mounted on both ends of a lower surface of the palm grasping member 70 for mounting a belt. The long holes 72 are one example of a structure in which the turning shaft 71 can displace with respect to the palm grasping member 70.

FIGS. 10 to 12 show a using state of the wrist assisting apparatus. FIGS. 10 and 11 show the palm-bending state, and FIG. 12 shows the backward-bending state.

The angle of the palm grasping member 70 can be changed in accordance with a wrist state of a user, and a position of the palm grasping member 70 can be adjusted in accordance with a hand size of the user. According to the embodiment, by the moving mechanism 11 that moves toward or away from the front arm, it is possible to eliminate such a sense of disharmony that a user feels as if his or her hand is pressed toward the front arm or pulled in a direction separating from the front arm.

As shown especially in FIG. 12, play between the apparatus and a hand can be eliminated when bending the wrist backward, and sufficient backward bending region can be secured.

Although the belt fixing tools 73 are provided on the lower surface of the palm grasping member 70 in this embodiment, the palm rest member 10 may be provided instead of the belt fixing tools 73. If a grip is fixed by the palm rest member 10 in addition to the belt, even if a grasping power is weakened, sufficient rehabilitation'effect can be obtained.

Although an opening of the front arm wearing tool 30 is oriented to the upper surface in this embodiment, the opening of the front arm wearing tool 30 may be oriented to the lower surface. In this case, the belt fixing tools 73 are disposed on the side of the opening of the front arm wearing tool 30. The opening of the front arm wearing tool 30 is oriented to the palm side, since the front arm wearing tool 30 is located on the back side of the front arm, play when backward bending can be reduced. When the opening of the front arm wearing tool 30 is oriented to the backhand side, it is easy to wear the apparatus and a natural using feeling can be obtained. If the palm grasping member 70 is attachable and detachable and the palm grasping member 70 can be attached to the angle changing member 20 from any of the upper surface side or the lower surface side, flexible wearing posture of the wrist assisting apparatus can be obtained.

In the present invention, since the joint member 40 has the above-described structure, even when the wrist assisting apparatus and the joint are deviated from each other in position, the joint member is deformed, the deviation is moderated and smooth motion can be secured.

In the invention, the angle changing members 20 are provided on the both sides of the palm rest member 10, the angle changing members 20 respectively have the joint members 40, and the joint members 40 are located on both sides of a wrist, thereby supporting the both sides of the wrist. Therefore, the wrist can smoothly move, and the wrist can strongly be held.

In the invention, the joint member 40 is used as the extension spring. Therefore, the joint member 40 vies with a shrinking force in an axial direction for compressing a wrist joint generated by a driving force generated by the actuator provided astride the wrist joint, it is possible to reduce an inhibition with respect to a torque for bending the wrist joint normally or backward, and the wrist joint can move smoothly.

In the invention, since the joint member 40 is used as the compression spring, a spring length becomes constant at the axis of the spring with respect to the normal or backward bending of the wrist. Therefore, if the axis is placed on the axis of the wrist joint, an influence of deviation with respect to bending in any direction can be suppressed to a low level, and the wrist joint can move smoothly. Further, since there is no contact between coils, even if the apparatus is repeatedly used for a long term, transmutation generated by rubbing between the coils can be suppressed.

In the invention, the front arm wearing tool 30 and the angle changing member 20 are connected to each other through the artificial muscle 50, the actuator that expands or contracts by supplying or discharging gas, liquid, or solid material, or a mixture thereof is used as the artificial muscle 50. Therefore, it is possible to realize a motion close to a human muscle, and a rehabilitation effect is enhanced.

In the invention, the first link member 60A that turns around the palm-side position 20A of the angle changing member 20, and the second link member 60B that turns around the backhand side position 20B of the angle changing member 20 are provided, the artificial muscles 50 are connected to an end of the first link member 60A and an end of the second link member 60B, respectively. With this, a wrist can smoothly bend toward both the palm side and the backhand side.

In the invention, mechanism members that are required for bending and stretching a wrist are disposed only on the side of the wrist, i.e., on the backhand side. Therefore, the wearing feeling is excellent, the palm can freely be used and thus, another training can be carried out at the same time.

The present invention can be utilized as the wrist assisting apparatus that assists a wrist motion.

What is claimed is:

1. A wrist assisting apparatus comprising:
    a palm support member for supporting a hand of a user;
    angle changing members connected to opposing sides of the palm support member;
    a front arm wearing tool adapted to be disposed along a front arm of the user;
    joint members provided with rotation shafts which turnably connect the angle changing members to the front arm wearing tool, the joint members adapted to be located on opposing sides of a wrist of the user;
    a first actuator and a second actuator for displacing the angle changing members with respect to the front arm wearing tool;
    wherein a connecting member is provided on the angle changing member on a side of the front arm;
    an end of the first actuator is connected to the front arm wearing tool;
    an other end of the first actuator is turnably connected to a palm-side position of the connecting member;
    an end of the second actuator is connected to the front arm wearing tool at a first fulcrum;
    an other end of the second actuator is turnably connected to backhand-side position of the connecting member at the second turning fulcrum; and
    an axis, connecting the first fulcrum of the front arm wearing tool of the second actuator to the second turning fulcrum of the angle changing member of the second actuator, does not move beyond the rotation shaft of the joint member.

2. The wrist assisting apparatus according to claim 1, wherein the palm support member is a palm rest member for supporting a side of a back of the hand.

3. The wrist assisting apparatus according to claim 1, wherein the palm support member is a palm grasping member for supporting a palm side of the hand.

4. The wrist assisting apparatus according to claim 1, wherein one of the actuators comprising an artificial muscle that expands and contracts at least in its longitudinal direction.

5. The wrist assisting apparatus according to claim 1, wherein two artificial muscles are used for each of the angle changing members to connect the front arm wearing tool to the angle changing member, and each actuator comprising the artificial muscle that expands and contracts at least in its longitudinal direction.

6. The wrist assisting apparatus according to claim 5, further comprising a first link member that turns around the palm-side position of the connecting member and a second link member that turns around the backhand-side position of the connecting member, wherein one of the artificial muscles is turnably connected to the first link member and the other artificial muscle is turnably connected to the second link member.

7. The wrist assisting apparatus according to claim 6, wherein the rotation shaft of the joint member is disposed closer to the front arm wearing tool than a phantom line connecting the palm-side position and the backhand-side position with each other.

8. The wrist assisting apparatus according to claim 1, further comprising a moving mechanism for moving the palm support member toward or away from the front arm wearing tool.

9. The wrist assisting apparatus according to claim 2, further comprising a belt provided on an upper surface of the palm rest member, and a moving mechanism for moving the belt toward or away from the front arm wearing tool.

10. The wrist assisting apparatus according to claim 3, further comprising a moving mechanisms for moving the palm grasping member toward or away from the front arm wearing tool, and turning shafts for changing angles of the palm grasping member with respect to the moving mechanisms are provided on both ends of the palm grasping member, and the turning shaft can displace with respect to the palm grasping member.

11. The wrist assisting apparatus according to claim 3, wherein a belt fixing tool is provided on an upper surface or a lower surface of the palm grasping member.

12. The wrist assisting apparatus according to claim 3, wherein a palm rest member is provided on an upper surface or a lower surface of the palm grasping member.

* * * * *